US012569504B2

(12) United States Patent
Terry et al.

(10) Patent No.: US 12,569,504 B2
(45) Date of Patent: Mar. 10, 2026

(54) PROCESS FOR CREATING A CANNABINOID PICO-EMULSION WITH ANTIBIOTIC PROPERTIES AND THE RESULTING PICO-EMULSION

(71) Applicants: Miles J. Terry, Sacramento, CA (US); Robert Myers, Chico, CA (US)

(72) Inventors: Miles J. Terry, Sacramento, CA (US); Robert Myers, Chico, CA (US)

( * ) Notice: Subject to any disclaimer, the term of this patent is extended or adjusted under 35 U.S.C. 154(b) by 0 days.

(21) Appl. No.: 19/206,261

(22) Filed: May 13, 2025

(65) Prior Publication Data

US 2025/0268924 A1     Aug. 28, 2025

Related U.S. Application Data

(63) Continuation of application No. 18/744,608, filed on Jun. 15, 2024.

(60) Provisional application No. 63/521,641, filed on Jun. 16, 2023.

(51) Int. Cl.
| | |
|---|---|
| *A61K 31/00* | (2006.01) |
| *A61K 9/107* | (2006.01) |
| *A61K 36/185* | (2006.01) |
| *A61K 47/26* | (2006.01) |

(52) U.S. Cl.
CPC .......... *A61K 31/658* (2023.05); *A61K 9/1075* (2013.01); *A61K 36/3482* (2024.05); *A61K 47/26* (2013.01)

(58) Field of Classification Search
None
See application file for complete search history.

(56) References Cited

U.S. PATENT DOCUMENTS

| | | | |
|---|---|---|---|
| 8,501,232 | B2 | 8/2013 | Talton et al. |
| 10,736,868 | B2 | 8/2020 | Keizer et al. |
| 10,959,971 | B2 | 3/2021 | Komorowski |
| 11,173,128 | B2 | 11/2021 | Sunderland |
| 11,285,184 | B2 | 3/2022 | Cheekoori |
| 11,426,362 | B2 | 8/2022 | Wright et al. |
| 11,712,430 | B2 | 8/2023 | Magdassi et al. |
| 12,290,543 | B1 | 5/2025 | Schaneville |
| 2020/0345657 | A1 | 11/2020 | Lurya et al. |
| 2021/0093559 | A1 | 4/2021 | Karolchyk |
| 2021/0177013 | A1 | 6/2021 | Jackowetz et al. |
| 2021/0361574 | A1 | 11/2021 | Sawyer |
| 2023/0000770 | A1 | 1/2023 | Tan et al. |
| 2023/0081357 | A1 | 3/2023 | Pacchetti et al. |
| 2023/0248690 | A1 | 8/2023 | Cheekoori |

FOREIGN PATENT DOCUMENTS

| | | | | |
|---|---|---|---|---|
| CA | 2692539 | A1 * | 1/2009 | .............. A61P 43/00 |
| EP | 3582750 | B1 | 7/2023 | |
| GB | 202205056 | A | 5/2022 | |
| WO | 2020000024 | A1 | 1/2020 | |
| WO | 2023194751 | A1 | 10/2023 | |

OTHER PUBLICATIONS

"PCT International Search Report in PCT/US2024/034235 dated Nov. 26, 2024, 3 pages".
Scianna, Tony, "Apex Labs CBD Introduces Pico IV CBD Isolate for IV Therapy", 1-2. Wellspa360. Web. Sep. 8, 2023; <Retrieved from the internet on Nov. 10, 2024<https://www.wellspa360.com/wellness/therapies/news/22872531/apex-labs-cbd-introduces-pico-ivcbd-isolate-for-iv-therapy>; p. 1>.
Zenith, "Bath Temperatures can Drastically Affect Cleaning Performance", 1-4. Zenith. Dec. 2020; < Retrieved from the internet on Nov. 12, 2024 <https://zenith-ultrasonics.com/temperature-effects/#: text=Temperature%20Above%2065%25%20of%20the, 130% 20and%20180%20degrees%20F>; p. 1>; <DOI: Web>.

* cited by examiner

*Primary Examiner* — Michael V Meller
(74) *Attorney, Agent, or Firm* — SERVILLA WHITNEY LLC

(57) ABSTRACT

A novel process of creating a cannabinoid pico-emulsion resulting in a sterile and injectable cannabinoid emulsion with increased bioavailability and antibiotic characteristics, and the resulting novel cannabinoid pico-emulsion, for the purpose of treating a wide variety of medical condition in both human and animals.

13 Claims, 5 Drawing Sheets

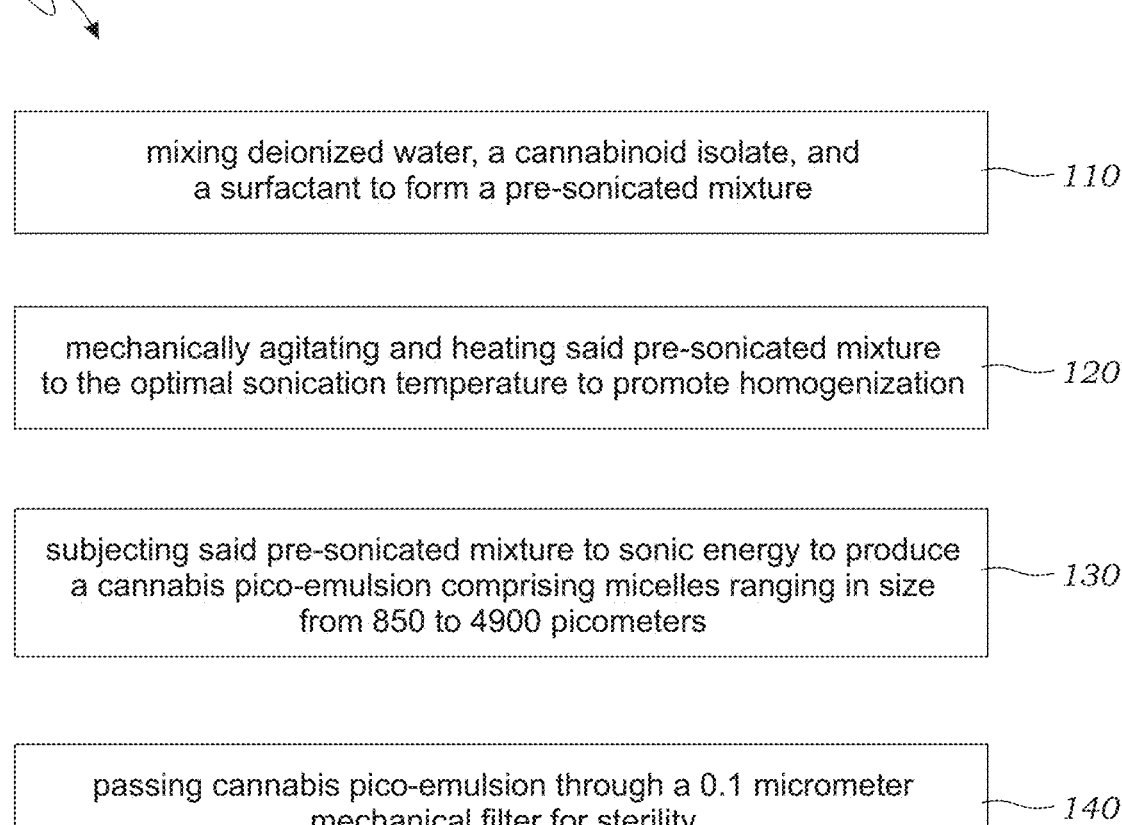

*100* mixing deionized water, a cannabinoid isolate, and a surfactant to form a pre-sonicated mixture — *110* mechanically agitating and heating said pre-sonicated mixture to the optimal sonication temperature to promote homogenization — *120* subjecting said pre-sonicated mixture to sonic energy to produce a cannabis pico-emulsion comprising micelles ranging in size from 850 to 4900 picometers — *130* passing cannabis pico-emulsion through a 0.1 micrometer mechanical filter for sterility — *140*

PROCESS FOR CREATING A CANNABINOID PICO-EMULSION WITH ANTIBIOTIC PROPERTIES AND THE RESULTING PICO-EMULSION

CROSS-REFERENCE TO RELATED APPLICATIONS

This United States Non-Provisional Utility Patent application claims the priority date of U.S. Provisional Application No. 63/521,641, titled: "CANNABINOID PICO EMULSION," filed Jun. 16, 2023 in the United States Patent and Trademark Office, the disclosure of which is hereby incorporated by reference in its entirety.

FIELD OF THE PRESENT DISCLOSURE

This disclosure relates generally to medical grade cannabinoid-based products, and more specifically to a process of creating a sterile and injectable cannabinoid pico-emulsion featuring increased bioavailability and antibiotic characteristics, and the resulting novel cannabinoid pico-emulsion.

BACKGROUND

As our understanding of the medicinal properties of *cannabis* continues to evolve, there has been a notable surge in the exploration and utilization of THC (tetrahydrocannabinol), CBD (cannabidiol), and other *cannabis*-derived compounds for various medical purposes, and with an expanding body of research providing scientific evidentiary support, *cannabis*-derived compounds are increasingly being integrated into mainstream medical protocols for treating a wide range of medical conditions.

Traditionally, the method of consumption or route of administration of *cannabis* has been limited to either smoking or ingesting edibles. While these legacy modes of administration offer certain benefits, they also come with notable drawbacks and limitations. For example, smoking *cannabis* involves the inhalation of smoke, which can irritate the respiratory system and includes other harmful byproducts of combustion that may pose risks to overall health over time. Further, some individuals may disfavor smoking as a route of administration because it necessarily exposes others in the immediate area to second hand smoke. Some of these concerns can be mitigated by the use of e-cigarettes or vaping; however, vaping is associated with various health risks as well. Smoking and vaping may also be disfavored by some individuals seeking to treat medical conditions with *cannabis* because such legacy delivery systems are traditionally associated with recreational *cannabis* use which may still be associated with stigmas and other various social sentiments, both positive and negative.

The introduction of *cannabis*-based compounds through the consumption edibles can be much more discreet than smoking or vaping but this route of administration is associated with its own limitations as well. For example, edibles are traditionally associated with delayed onset of effects and unpredictable potency, making it challenging to control dosage and very difficult to achieve immediate effects. One reason for the challenges related to predicting potency when ingesting *cannabis*-based compounds is that the digestive tract metabolizes THC, CBD, and other cannabinoids before they can reach the bloodstream. This process, known as first-pass metabolism, reduces the amount of the desired cannabinoid that ultimately enters the bloodstream, leading to decreased bioavailability and potentially requiring higher initial doses to achieve the desired effects.

Additionally, when THC is metabolized, it can produce metabolites such as 11-hydroxy-THC (also known as Delta-11) and Delta-10-THC, which may remain in the body for longer periods than THC itself. This prolonged presence of metabolites can increase the risk of failing a drug test even when the psychoactive effects of the THC, or other desired effects of the target cannabinoid, have subsided presenting an unnecessary concern for individuals using *cannabis* for medical purposes.

Recognizing the limitations of legacy delivery methods, there is a growing interest in alternative routes of administration that offer enhanced dosing precision, immediate bioavailability, and therapeutic efficacy. One such approach is the development of injectable or intravenous formulations of *cannabis*-derived compounds. By administering cannabinoids directly into the bloodstream, injectable formulations bypass the digestive system and liver metabolism, leading to faster onset of action and increased bioavailability compared to legacy modalities.

Moreover, injectable *cannabis* formulations offer the potential for more precise dosing, allowing healthcare providers to more precisely tailor treatment regimens to individual patients' needs. This can be particularly beneficial for conditions requiring rapid symptom relief or for patients with lung or gastrointestinal issues that may impair or limit absorption into the bloodstream by legacy routes of administration.

One important parameter when developing an injectable or intravenous *cannabis* formulations is emulsion droplet or micelle size. Generally speaking, the smaller the droplet size, the greater the bioavailability.

Some researchers have also attempted to achieve greater cannabinoid bioavailability by altering the polarity of the cannabinoid molecule to increase its solubility through glycosylation. Glycosylation is the process of attaching a sugar molecule (a glycan) to the cannabinoid molecule. This modification can improve the cannabinoid's solubility in water, thus potentially providing a cannabinoid solution featuring an evenly distributed, highly bioavailable molecule eliminating the need for surfactants and emulsifications all together; however, the glycogen group also typically alters the manner in which the cannabinoid interacts with the body's endocannabinoid receptors, which, in turn, alters the cannabinoid's effect on the body and its resulting medical benefits. Thus, while glycosylation of cannabinoids may still prove useful for certain functions, to date, the medical benefits have been much more limited than with cannabinoid emulsifications. There still exists a need to produce an cannabinoid emulsion with the smallest droplet or micelle size possible.

Several pharmaceutical developers have been successful achieving methods of creating cannabinoid emulsions with droplets in the nanometer range such as the methods described in United States utility U.S. Pat. No. 10,738,268, titled *Cannabis* Nano-Emulsion Methods; however, to date, such legacy methods have not been successful in yielding a stable cannabinoid emulsion in the picometer range.

And, while advances in cannabinoid nano-emulsions have garnered substantial attention and traction within scientific discourse, there is general consensus among pharmaceutical developers that there are still greater advantages that could be realized by developing a stable cannabinoid emulsion in the picometer range. The most predictable advantage being that, as with almost all emulsions of an active ingredient, bioavailability will likely continue to increase as the droplets or micelles trend smaller due to the increased surface area. However, there may also be additional less-predictable advantages as well, such as antibacterial and/or antibiotic properties of finer cannabinoid emulsions, especially in relation to gram-negative bacteria.

Despite the consensus that a stable cannabinoid pico-emulsion would be beneficial and worth pursuing, prior to this present disclosure, none have been successful in developing a method of producing such an emulsion because creating an emulsion with droplets or micelles in the picometer range involves overcoming several formidable technical challenges.

One such technical challenge to developing a finer emulsion is related to the nature of the component ingredients. Many legacy emulsions call for the combination of one or more cannabinoid oils and a surfactant; however, most cannabinoid oils also contain a broad array of compounds other than the cannabinoid oil itself. These additional compounds range from natural phytochemicals, such as various terpenes and flavonoids, to residual solvents left over from extraction, and/or other totally foreign impurities. Many of these additional compounds disrupt the bonding of the intended cannabinoid oil and surfactant which can, directly or indirectly, impact the resultant emulsion's droplet or micelle stability and size.

Such disruptions make it unnecessarily difficult to produce a stable pico-emulsion of cannabinoid oils, thus, the challenge of producing a finer cannabinoid oil emulsion can be partially mitigated by simply beginning the process with higher purity ingredients. There exists a need to address this and other technical challenges of producing a finer cannabinoid emulsion because the therapeutic advantages of developing a stable cannabinoid pico-emulsion is readily apparent and significant.

The present disclosure distinguishes over the prior art providing heretofore unknown advantages as described in the following summary.

BRIEF SUMMARY OF THE DISCLOSURE

The present disclosure describes a novel process for creating a sterile and injectable cannabinoid pico-emulsion featuring increased bioavailability and antibiotic characteristics for the use in treating a wide variety of medical conditions.

The sterile and injectable cannabinoid pico-emulsion resulting from this novel process features emulsified droplets or micelles ranging in size from about 4900 picometers down to about 850 picometers. In one embodiment, the emulsified droplets or micelles range in size from about 4000 picometers down to about 850 picometers. This pico-emulsion provides significantly enhanced bioavailability over legacy cannabinoid nano-emulsions and exhibits potent antibiotic properties, particularly against gram-negative bacteria, which are known for their resistance to conventional antibiotics.

Previous efforts in the pharmaceutical industry to develop cannabinoid emulsions have been able to achieve emulsified droplets of the dispersion phase as small as about 5 nanometers, but producing stable cannabinoid emulsions with droplets in picometer range have proven to be an insurmountable challenge due to several technical hurdles. The presently disclosed novel process includes several innovations that have, together, overcome these previously intractable challenges. Such innovations include, the use of cannabinoid isolates with purity of about 99% rather than full spectrum cannabinoid oils, the intentional over-saturation of a surfactant, by about 5%, with the Hydrophilic-Lipophilic Balance (HLB) number of about 15; polysorbate 80 being a preferred surfactant. In one embodiment, the HLB is 15, while in others embodiments, the HLB falls within a range of about 14.9 to 15.1.

Surfactants play a role in emulsion chemistry by decreasing the interfacial tension between two immiscible fluids, such as water and oil. A surfactant's unique structure, featuring both hydrophobic and hydrophilic extremities, allows the molecule to both surround and bond with a droplet of the dispersed phase (in this case oil) and, on its opposing extremity, simultaneously bond with the continuous phase (in this case deionized water). This dual interaction integrates droplets of the previously immiscible fluid into the continuous phase to form what appears on the macro-level to be a homogenous fluid.

An important characteristic of a surfactant is the strength with which the hydrophilic extremity (water attracting) and lipophilic extremity (oil attracting) attracts the molecules to which they have affinity. Surfactants are categorized by their comparative hydrophilic-hydrophobic affinity by a unitless number on a scale from 0 to 20 called the hydrophilic-lipophilic balance number or HLB. The presently disclosed process and product by process requires a surfactant with a HLB number of about 15, such as polysorbate 80. In another embodiment, the presently disclosed process and product by process requires a surfactant with a HLB number of 15, while in other embodiments a surfactant with a HLB number between about 14.9 to about 15.1 may be used. An HLB number in this range indicates a strong hydrophilic character making it very well suited for an oil-in-water emulsion (as opposed to water-in-oil emulsion). The strength of the hydrophilic nature of a surfactant with an HLB of about 15 is ensures stability by preventing the oil and water phases from separating over time.

Stability is particularly important when trying to achieve a highly fine dispersion such as a pico-emulsion because when emulsions become unstable, the micelles have a tendency to recombine to form larger ones, driven by a natural tendency to achieve a lower thermodynamic energy state. This process is called the Oswalting effect. The Oswalting effect occurs more prevalently when the surfactant has insufficient bonding strength to remain affixed to either the dispersed or continuous phase, or both. This can also occur when there exists excessive amounts of impurities that disrupt the bonding of the surfactant and/or an insufficient quantity of surfactant to create a complete monolayer of coverage across the entire outer surface of each droplet to form a complete micelle. This novel process mitigates against the Oswalting effect by ensuring both that the initial mixture of ingredients is adequately saturated with surfactant and that all component ingredients are about 99% pure cannabinoid isolate.

The process begins with the use of a cannabinoid isolate that is at least about 99% pure, or stated another way, a cannabinoid isolate with no more than about 10,000 ppm of impurities, which is significantly higher than the purity of the cannabinoid oils used in legacy methods. Typical cannabinoid oils, sometimes called full-spectrum cannabinoid oils, often contain a wide variety of impurities, including terpenes, flavonoids, solvents left over from extraction, and other both naturally occurring and foreign contaminants that can interfere with the bonding between the cannabinoid oil and the surfactant complicating the formation of a stable micelles as previously discussed. By starting with a highly pure cannabinoid isolate rather than cannabinoid oil, these potential complications can be substantially reduced.

The cannabinoid isolate can be an isolate selected from a wide range of cannabinoid oils, or an isolate derived from multiple cannabinoid oils combined. The following is a non-exclusive list of the cannabinoid oils from which the cannabinoid oil isolate can be derived: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV), Delta-8-tetrahydrocannabinol (48-THC), Delta-8-tetrahydrocannabinolic acid (48-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), and OH-iso-HHCV.

Another component to ensuring micelle stability in the picometer range is the introduction of a sufficient quantity of the of surfactant. The precise theoretical amount of surfactant necessary can be calculated by first determining the theoretical total surface area of the desired quantity of cannabinoid isolate intended to be emulsified if such quantity was divided into spherical droplets of the target size. This calculation can be made using the following equation:

$$Aoil = \frac{3 * Voil}{r}$$

Where:

$A_{oil}$=total surface area of the oil droplets;

$V_{oil}$=volume of the oil phase;

r=radius of the oil droplets.

Then the quantity of surfactant required to create a single monolayer of surfactant coverage of the theoretical total surface area of the all of the spherical oil droplets can be calculated by dividing the previously calculated total surface total surface area ($A_{oil}$) by the surface coverage of the selected surfactant ($A_s$) (the surface coverage area of a single molecule of the selected surfactant is typically found in chemistry literature).

The calculation can be made with this equation:

$$Nsurf = \frac{Aoil}{As}$$

Where:

$N_{surf}$=number of surfactant molecules required;

$A_{oil}$=total surface area of the oil droplets;

$A_s$=area covered by one molecule of surfactant.

Then the previous calculated total number of surfactant molecules required to create a single monolayer over the total surface area of the all of the spherical oil droplets ($N_{surf}$) can then be converted to a more meaningful number by dividing it by Avogadro's number and multiplying it by the molar mass of the selected surfactant using the following equations:

$$Nmoles = \frac{Nsurf}{Na}$$

$$Msurf = Nmoles * Mmolar$$

Where:

$N_{surf}$=number of surfactant molecules required;

Na=Avogadro's number $6.022 \times 10^{23}$ $N_{moles}$=number of surfactant moles required;

$M_{molar}$=molar mass of the surfactant $M_{surf}$=mass of surfactant required surfactant.

The result of this calculation provides the theoretical minimum quantity of surfactant required to provide a single monolayer of surfactant coverage if the droplets of the dispersed phase are of the theoretical size in terms of mass of surfactant; however, if the actual droplets are smaller than the theoretical size then total surface area of the droplets may be nominally larger. To ensure sufficient surfactant is available, the calculated quantity mass of surfactant should be increased by about 5% to intentionally oversaturate the dispersed phase. The intentional over-saturation ensures stability for achieving and maintaining a stable cannabinoid pico-emulsion.

Once the desired quantity of cannabinoid isolate and the corresponding amount of surfactant is calculated. The two components are mixed with deionized water and heated to a temperature between about 140 to about 200 degrees Fahrenheit and stirred or otherwise mechanically agitated to achieve maximum pre-sonication homogenization. In another embodiment the two components are mixed with deionized water and heated a temperature within about 10 degrees of the newly formed mixture's boiling point.

Once preheated and thoroughly stirred, the pre-sonicated mixture is subjected to sonic energy at a frequency greater than 60 kHz, such as between about 60 kHz and about 80 KHz, with a sufficient energy to generate the shear force necessary to break-up the droplets of dispersed phase into smaller droplets. This sonication process should continue until the micelles reach a size between about 4900 and 850 picometers. The size distribution of the micelles is confirmed via one of several technologies such as using Dynamic Light Scattering (DLS), which should show a consistent distribution because an emulsion in the picometer range should appear transparent; however, there may be very minimal spikes indicating the presence of any remaining impurities. Other technologies that may be used to confirm that a cannabinoid pico-emulsion with micelles in the desired size range has been achieved are Small-Angle X-ray Scattering (SAXS) or Nuclear Magnetic Resonance (NMR) Spectroscopy.

To ensure sterility, the resulting emulsion is passed through a 0.1 micron mechanical filter. This filtration step is designed to remove any potential bacterial contamination but is also effective at confirming that no large inorganic particles impurities have compromised the emulsion.

A primary advantage of this pico-emulsion over existing legacy cannabinoid nano-emulsions is its dramatically increased bioavailability, which is particularly important for medical applications where the efficiency of drug delivery can significantly impact therapeutic outcomes. Smaller micelles allow for faster and more efficient absorption into the bloodstream, leading to quicker onset of action and more precise dosing.

However, as previously stated, in addition to the enhanced bioavailability, the pico-emulsion exhibits significant antibiotic properties, especially against gram-negative bacteria infection on both animals and humans. Gram-negative bacteria pose a substantial challenge in the medical field due to their robust resistance to traditional antibiotics. These bacteria have an outer membrane that is particularly effective at preventing the entry of harmful substances, including many antibiotics, detergents, and other antimicrobial agents. This resistance is primarily due to the structure of their cell wall, which includes a thick peptidoglycan layer sandwiched between an inner and outer cytoplasmic membrane.

The novel pico-emulsion's effectiveness against gram-negative bacteria is attributed to the incredibly small size of the micelles, which can penetrate the bacteria's outer membrane through the gram-negative bacteria's porin sites, which are the small portals through which the gram-negative bacteria transport molecules across their outer membrane, such as nutrients and metabolites. The bacteria's porin sites typically range in size between 1000 to 2000 picometers which is large enough for many of the micelles of a pico-emulsion created by the presently disclosed procedure to enter; thereby, bypassing the bacteria's protective outer membrane.

Further, many times when micelles reach the picometer size range their shape is not spherical as was assumed when making the theoretical calculations. Due to the bonding forces of the surfactant and other parameters such as the shape of the dispersed phase molecules, micelles in the picometer range often take of an highly elongated, rod-like configuration. Such a configuration may further enable larger micelles to enter the bacteria porin sites when their narrow dimension is properly aligned with respect to the porin site.

Once a micelle is inside the bacterium, the surfactant's bond with the dispersed phase is disturbed, whether such disturbance is due to the bacterium attempting to metabolize the micelle or some other mechanical or chemical influence, the stability of micelles tend to degrade once inside thereby allowing for the Oswalting effect to commence and the micelles to combine and grow, eventually the size of the combined micelles will physically rupture the gram-negative bacterium's cell membrane causing its demise.

The significance of this discovery cannot be overstated. Gram-negative bacteria are often multidrug-resistant (MDR) or extensively drug-resistant (XDR), making them a leading cause of severe and hard-to-treat infections which can be fatal. The ability of cannabinoid pico-emulsions to effectively combat these bacteria offers a promising new therapeutic approach, potentially reducing reliance on traditional antibiotics.

This novel process and resulting product not only offers significantly enhanced bioavailability, and, as previously mentioned, the advantages extend beyond the realm of bioavailability to embrace the burgeoning field of antimicrobial therapeutics, wherein *cannabis* pico-emulsions emerge as a potent weapon against antibiotic-resistant pathogens. Of particular salience is their efficacy against gram-negative bacteria, a cohort notorious for its recalcitrance to traditional antibiotics. Leveraging the inherent antibacterial properties of *cannabis*-derived compounds, which have been limited in application as described above, pico-emulsions now furnish a multifaceted approach to combating gram-negative bacterial infection, thereby improving both patient outcomes and public health outcomes at large.

Thus, the imperative of transcending the confines of nano-emulsion technology is underscored by the latent advantages offered by pico-emulsions, from heightened bioavailability to enhanced antimicrobial efficacy. By surmounting the technical hurdles inherent in particle size reduction and impurity mitigation, researchers stand poised to unlock the full therapeutic potential of *cannabis*-derived compounds, thereby heralding a new epoch in medical science.

This disclosure teaches certain benefits in construction and use which give rise to the objectives described below:

A primary objective inherent of the above described disclosure is to provide a process for creating a sterile and injectable cannabinoid pico-emulsion;

Another objective of the above described disclosure is to provide a process for creating a cannabinoid pico-emulsion with greater bioavailability;

A still further objective of the above described disclosure is to provide a process for creating a cannabinoid pico-emulsion with antibiotic characteristics;

A yet still further objective of the above described disclosure is to provide the cannabinoid pico-emulsion product that results from the disclosed process;

A yet still further objective is to provide a cannabinoid pico-emulsion for the use as a medicament, and/or for use in the preparation of medicaments, for treatment of medical conditions; and A yet still further objective is to provide a cannabinoid pico-emulsion for the use as a Medicaments, and/or for the use in preparation of medicaments, for treatment of gram-negative bacterial infections;

Other features and advantages of the present disclosure will become apparent from the following more detailed descriptions, taken in conjunction with the accompanying drawings, which illustrate, by way of example, the principles and features of the presently described process.

BRIEF DESCRIPTION OF THE SEVERAL VIEWS OF THE DRAWINGS

The accompanying drawings illustrate various exemplary implementations and are part of the specification. The illustrated implementations are proffered for purposes of example not for purposes of limitation. Illustrated elements will be designated by numbers.

Once designated, an element will be identified by the identical number throughout. Illustrated in the accompanying drawing(s) is at least one of the best mode embodiments of the present disclosure. In such drawing(s):

FIG. 1 is a flowchart describing a process for creating a sterile and injectable cannabinoid pico-emulsion featuring increased bioavailability and antibiotic characteristics.

Figure 2:
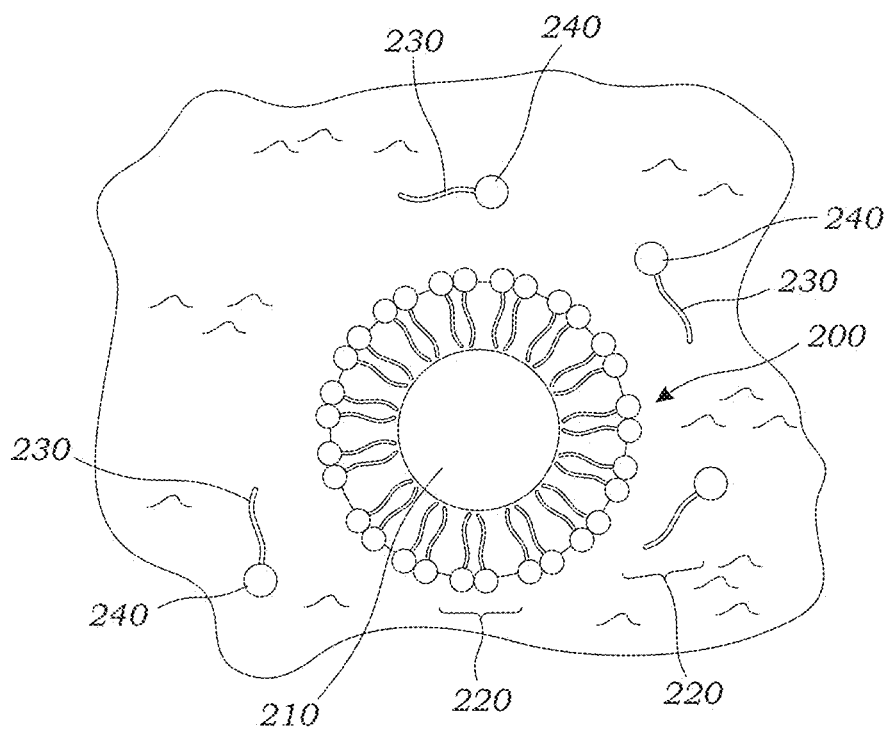

FIG. 2 is a conceptual diagram illustrating an micelle in a *cannabis* pico-emulsion featuring a droplet of cannabinoid oil sequestered by the hydrophobic tails of a plurality of amphiphilic surfactant molecules while the hydrophilic heads of such molecules are in contact with the surrounding continuous phase.

Figure 3:
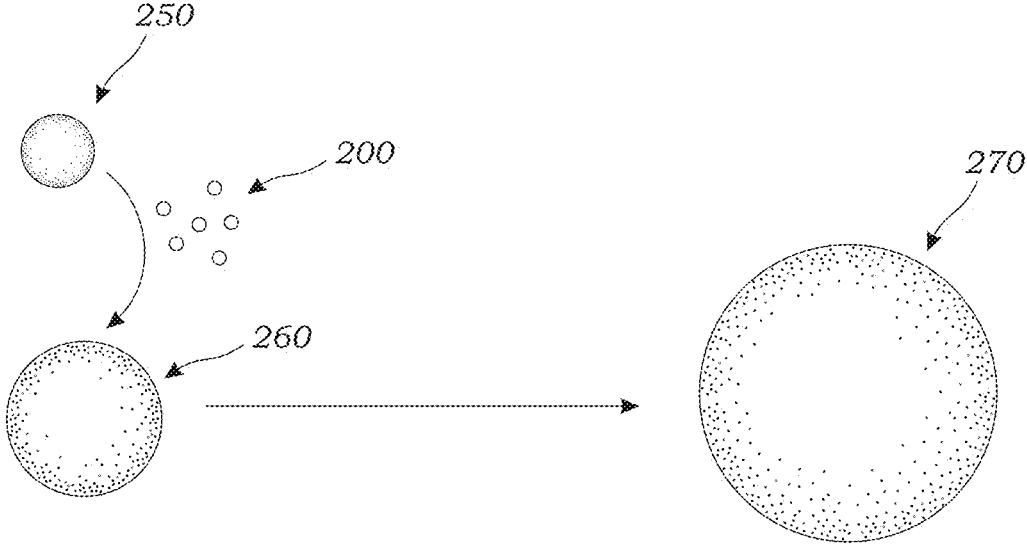

FIG. 3 is a conceptual diagram illustrating the thermodynamically-driven phenomena called Oswalt ripening in which several smaller micelles in an emulsion combine to form a single larger, more energetically favorable micelle.

Figure 4:
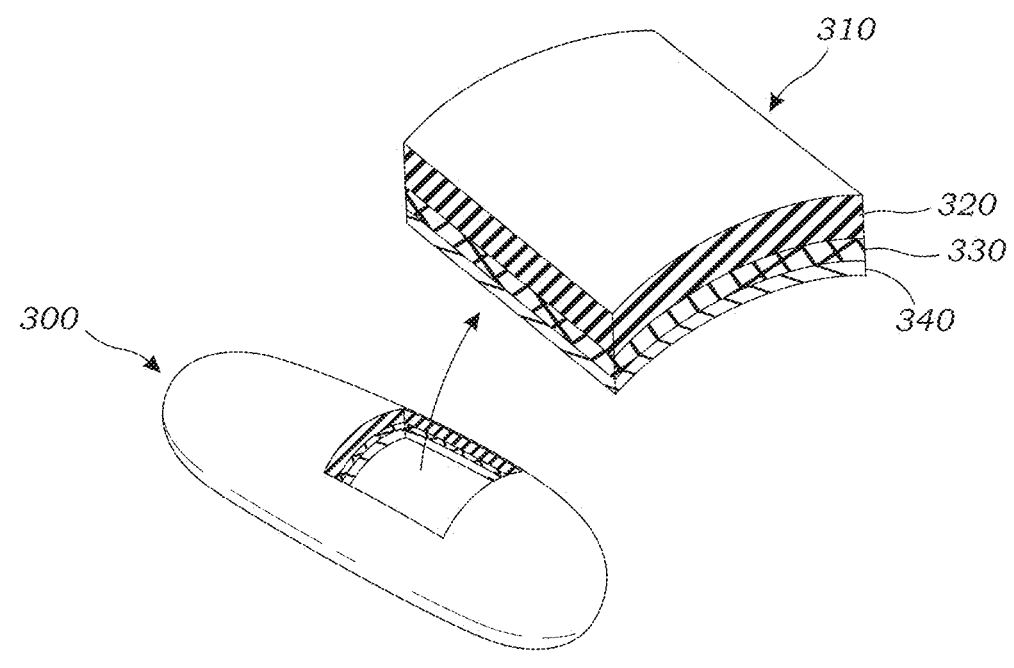

FIG. 4 is an exploded cutaway view of a conceptual diagram of a gram-negative bacterium featuring it's characteristic cell wall, which consists of a thin peptidoglycan layer between an inner and an outer cytoplasmic membrane.

Figure 5:
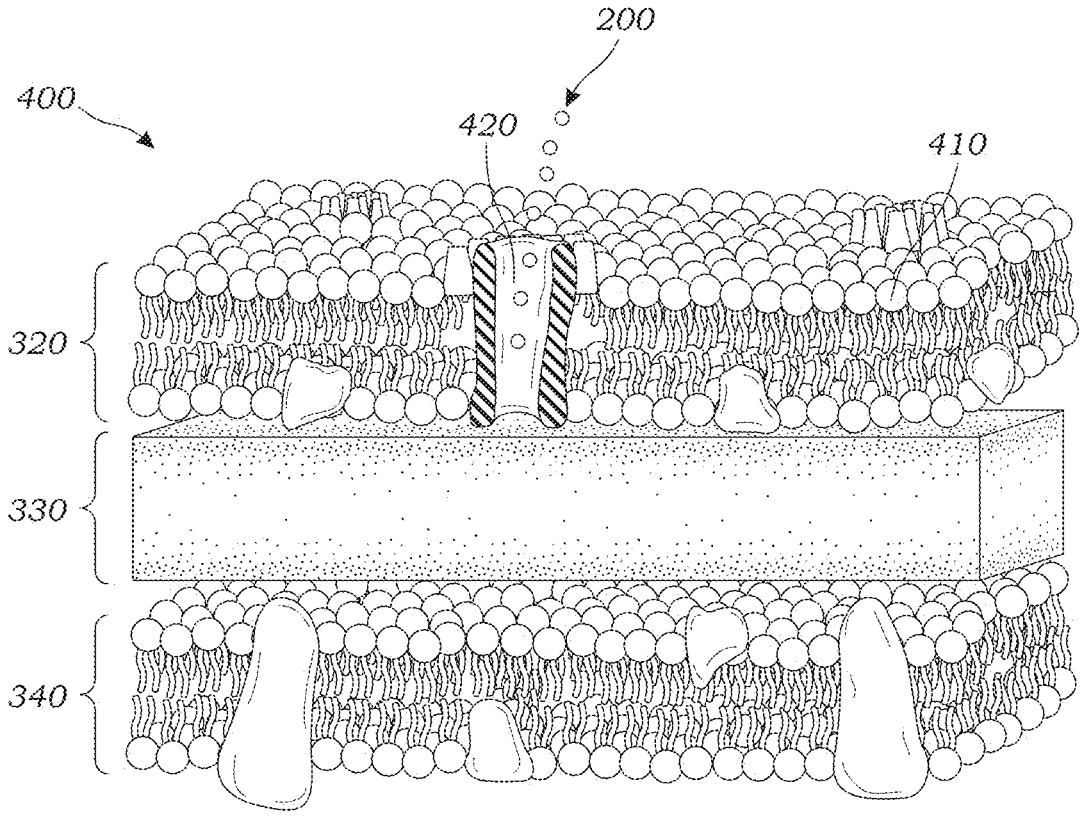

FIG. 5 is a conceptual cutaway diagram of the characteristic cell wall of a gram-negative bacterium, including a porin site which is a feature in the outer cytoplasmic membrane through which gram-negative bacterium mediate diffusion of small hydrophilic molecules.

Figure 6:
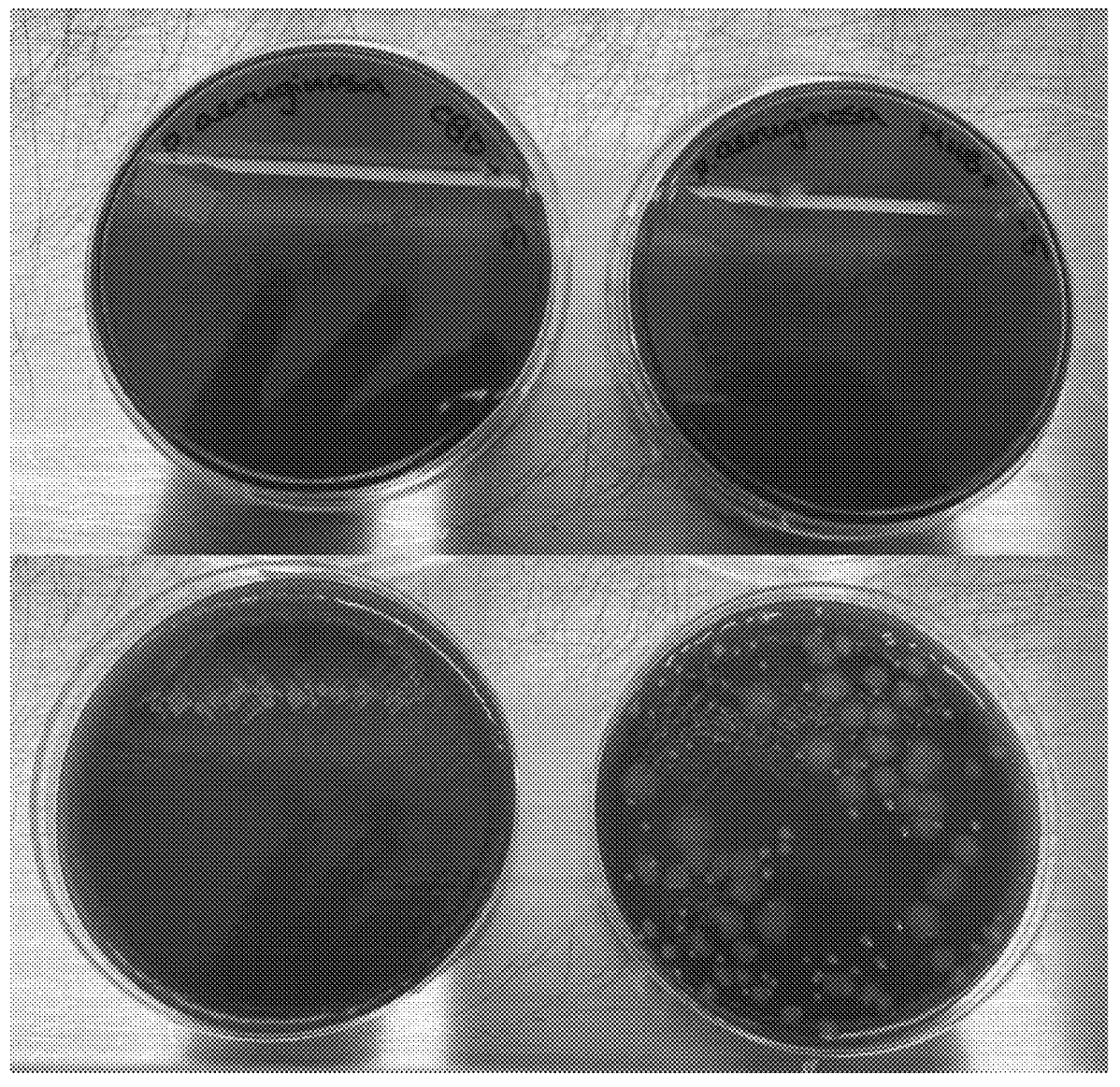

FIG. 6 is a comparative culture of the gram-negative bacteria, *Pseudomonas aeruginosa*, with and without exposure to the presently disclosed cannabinoid pico-emulsion.

Figure 7:
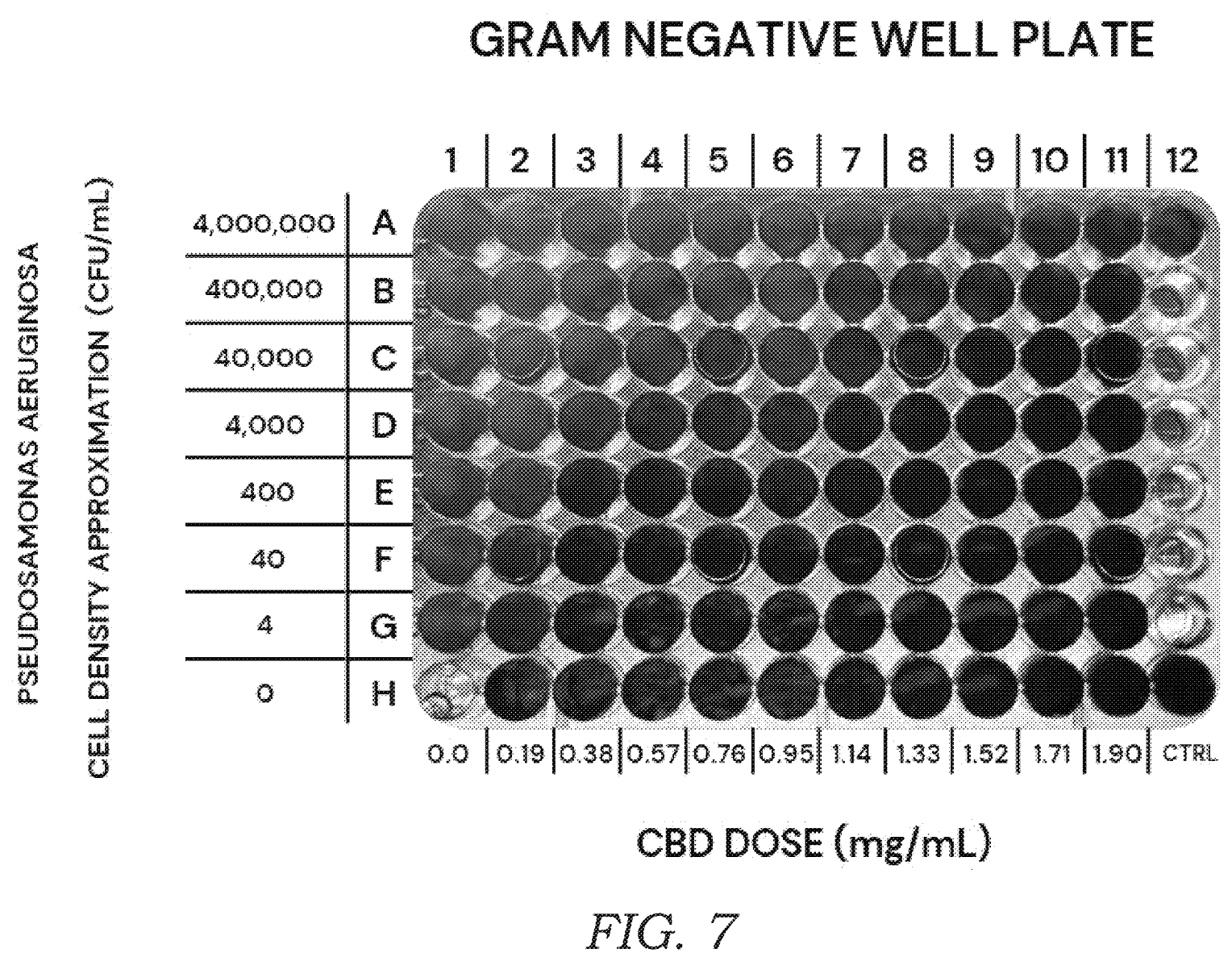

FIG. 7 is a comparative array of the gram-negative bacteria, *Pseudomonas aeruginosa*, of various growth density exposed to various concentrations of the presently disclosure cannabinoid pico-emulsion.

DETAILED DESCRIPTION OF THE EXEMPLARY EMBODIMENTS

The above described drawing illustrate multiple exemplary embodiments of the presently disclosed process and its many features in at least one of its preferred, best mode embodiments, which is further defined in detail in the following description. Those having ordinary skill in the art may be able to make alterations and modifications to what is described herein without departing from its spirit and scope of the disclosure. Therefore, it must be understood that what is illustrated is set forth only for the purposes of example and that it should not be taken as a limitation in the scope of the present process or its many features.

Described now in detail is a novel process for creating a sterile and injectable cannabinoid pico-emulsion featuring increased bioavailability and antibiotic characteristics for the use of treating a wide variety of medical conditions.

FIG. 1 illustrates an exemplary embodiment of a flowchart setting forth the basic the steps in the presently disclosed process 100. It begins with combining one or more cannabinoid isolates with a carefully calculated amount of surfactant. The surfactant should have a hydrophilic-lipophilic balance (HLB) number of about 15, preferably polysorbate 80, and deionized water 110. In another embodiment, the HLB is about 14.9 to about 15.1. An HLB number of about 15 indicates a strong hydrophilic character making it very well suited for an oil-in-water emulsion (as opposed to water-in-oil emulsion). Then the pre-sonicated mixture is stirred or otherwise mechanically agitated and heated to between 140 to 200 degrees Fahrenheit 120. Once the pre-sonicated mixture is brought up to temperature and thoroughly blended, the pre-sonicated mixture is bombarded with sonic energy of a frequency greater than 60 kHz, such as between 60 and 80 KHz. The bombardment should continue until such time as the dispersed phase has formed micelles in the range 4900 to 850 picometers in diameter 130, and finally, the resulting pico-emulsion is passed through a 0.1 micron mechanical filter to sterilize the emulsion and remove any large impurities 140.

FIG. 2 is a conceptual drawing 200 of a droplet of the dispersed phase (the cannabinoid isolate) 210 sequestered by a plurality of surfactant molecules 220 featuring a hydrophilic head 240 and a lipophilic tail 230. The lipophilic tails 230 each bond to the cannabinoid isolate 210 and the hydrophilic heads 240 each bond to the continuous phase (the deionized water); thereby decreasing the interfacial tension between the dispersed and continuous phases.

FIG. 3 is a conceptual illustration of the Oswalting effect whereby the smallest sized droplets (perhaps picometer sized) 200 of a dispersed phase tend to combine with and contribute to the growing size of slightly larger sized droplet 250, which again tend to combine with even larger droplets 260, and even larger droplets 270. This phenomena is driven by thermodynamic forces of surface tension and the fact that larger droplet are a lower energy state. In order to create a stable pico-emulsion this tendency has to be prevented, which highlights the proper selection of the appropriate surfactant and the use of a sufficient amount of such surfactant.

FIG. 4 is perspective conceptual drawing an exemplar gram-negative bacterium 300 with an exploded cutaway section 310 illustrating the complex multi-layer cell wall comprised of a peptidoglycan cell wall 330 between two an inner and outer cytoplasmic membrane 320, 340. It is this complex structural barrier that enables gram-negative bacteria 300 to be resistant to many traditional antibiotic and makes infections of gram-negative bacteria 300 particularly problematic.

FIG. 5 is perspective conceptual drawing of cross-section of the cell wall of a gram-negative bacterium 400. The diagram illustrated the peptidoglycan layer 330 flanked by both an outer cytoplasmic membrane 320 and an inner cytoplasmic membrane 320 comprised of phospholipids 410, and, most importantly for the present disclosure, the porin site 420 through which gram-negative bacteria regulate molecule uptake. It is through the porin site 420 that a picometer sized cannabinoid micelle 200 can gain entry passed the protective outer layers and potentially cause the demise of the bacterium. In the drawing, the picometer sized cannabinoid micelles 200 are depicted as spherical. It is important to note that when cannabinoid micelles 200 reach such a diminutive sizes there shape is dictated by the various bonding forces of the surfactant which causes the micelles to assume an elongated shape.

FIG. 6 is a comparative culture of the gram-negative bacteria, *Pseudomonas Aeruginosa*. The upper two images are photographs of the bottom of the petri dishes 500 identifying the starting conditions while the bottom two photographs show the resultant bacterial growth. The petri dish 500 on the left was exposed to the presently disclosed cannabinoid pico-emulsion while the petri dish 500 on the right was not. It is visually apparent that the bacterial growth 510 was significantly inhibited by the cannabinoid pico-emulsion.

FIG. 7 is a comparative array of the gram-negative bacteria, *Pseudomonas aeruginosa*, of various growth density exposed to various concentrations of the presently disclosure cannabinoid pico-emulsion. In the array, the concentration of cannabinoid pico-emulsion is increased along the x-axis and the density of bacteria is increased along the y axis. The presence of the bacteria is indicated by a bright pink color and the absence of bacteria is indicated by a dark purple color. It is visually apparent that as the density of cannabinoid pico-emulsion is increased the bacteria survival decreases.

The embodiments described in detail above are considered novel over the prior art The words used in this specification to describe the instant embodiments are to be understood not only in the sense of their commonly defined meanings, but to include by special definition in this specification: structure, material, or acts beyond the scope of the commonly defined meanings. Thus, if an element can be understood in the context of this specification as including more than one meaning, then its use must be understood as being generic to all possible meanings supported by the specification and by the word(s) describing the element.

The definitions of the words or drawing elements described herein are meant to include not only the combination of elements which are literally set forth, but all similar structures, materials or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, substitutions, now or later known to one with ordinary skill in the art, are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. Sterile cannabinoid micelles in a pico-emulsion suitable for intravenous use in humans, wherein the sterile cannabinoid micelles in the pico-emulsion consist essentially of one or more cannabinoids covered by only one surfactant consisting of polysorbate 80, wherein the one or more cannabinoids are selected from the group consisting of purified Cannabichromene (CBC), purified Cannabinol (CBN), purified Cannabidiolic acid (CBDA), purified Cannabigerol (CBG), purified Cannabigerolic acid (CBGA), and combinations thereof, wherein the micelles are dispersed in water, and wherein the micelles are from about 850 picometers to about 4900 picometers.

2. The sterile cannabinoid micelles in a pico-emulsion of claim 1, wherein the one or more cannabinoids consist essentially of purified Cannabichromene (CBC).

3. The sterile cannabinoid micelles in a pico-emulsion of claim 1, wherein the one or more cannabinoids consist essentially of purified Cannabinol (CBN).

4. The sterile cannabinoid micelles in a pico-emulsion of claim 1, wherein the one or more cannabinoids consist essentially of purified Cannabidiolic acid (CBDA).

5. The sterile cannabinoid micelles in a pico-emulsion of claim 1, wherein the one or more cannabinoids consist essentially of purified Cannabigerol (CBG).

6. The sterile cannabinoid micelles in a pico-emulsion of claim 1, wherein the one or more cannabinoids consist essentially of purified Cannabigerolic acid (CBGA).

7. The sterile cannabinoid micelles in a pico-emulsion of claim 1, wherein the one or more cannabinoids consist essentially of purified Cannabidiolic acid (CBDA), purified Cannabigerol (CBG) and purified Cannabigerolic acid (CBGA).

8. The sterile cannabinoid micelles in a pico-emulsion of claim 1, wherein the one or more cannabinoids consist essentially of purified Cannabichromene (CBC), purified Cannabinol (CBN), purified Cannabidiolic acid (CBDA), purified Cannabigerol (CBG) and purified Cannabigerolic acid (CBGA).

9. The sterile cannabinoid micelles in a pico-emulsion of claim 1, wherein the one or more cannabinoids are at least 99% pure.

10. Sterile cannabinoid micelles in a pico-emulsion suitable for intravenous use in humans, wherein the sterile cannabinoid micelles in the pico-emulsion consist essentially of cannabinoids covered by only one surfactant consisting of polysorbate 80, wherein the cannabinoids consist of purified Cannabichromene (CBC), purified Cannabidiol (CBD), purified Cannabinol (CBN), purified Cannabidiolic acid (CBDA), purified Cannabigerol (CBG), and purified Cannabigerolic acid (CBGA), wherein the micelles are dispersed in water, and wherein the micelles are from about 850 to about 4900 picometers.

11. The sterile cannabinoid micelles in a pico-emulsion of claim 10, wherein the cannabinoids are at least 99% pure.

12. Sterile cannabinoid micelles in a pico-emulsion suitable for intravenous use in humans, wherein the sterile cannabinoid micelles in the pico-emulsion consist essentially of cannabinoids covered by only one surfactant consisting of polysorbate 80, wherein the cannabinoids consist of purified Cannabidiol (CBD), purified Cannabidiolic acid (CBDA), purified Cannabigerol (CBG), and purified Cannabigerolic acid (CBGA), wherein the micelles are dispersed in water, and wherein the micelles are from about 850 to about 4900 picometers.

13. The sterile cannabinoid micelles in a pico-emulsion of claim 12, wherein the cannabinoids are at least 99% pure.

* * * * *